Jan. 24, 1956 R. S. MOORE Plant Pat. 1,451

ROSE PLANT

Filed Jan. 18, 1955

WITNESS

Addison F. Avery

INVENTOR

Ralph S. Moore

Webster & Webster

ATTYS.

United States Patent Office

Plant Pat. 1,451
Patented Jan. 24, 1956

1,451

ROSE PLANT

Ralph S. Moore, Visalia, Calif.

Application January 18, 1955, Serial No. 482,689

1 Claim. (Cl. 47—61)

This invention relates to a new and distinct variety of rose plant which is a miniature, ever-blooming climber; this characteristic being a major feature of novelty.

The present variety of rose plant has growth and blooming habits generally similar to the climbing hybrid tea rose "High Noon," but is distinctive in that here the variety is a miniature climbing rose and bears pink instead of yellow flowers.

Other important characteristics of the instant variety of rose plant are substantially perfectly shaped buds; long lasting buds and flowers, both on the plant and when cut for ornamental display; color stability; and ease of propagation, both by budding and cuttings.

Further, the present variety is characterized by a healthy and vigorous plant, and by the habit of beginning to bloom when the plant is only six to eight inches high.

This variety of rose plant was originated by me in my nursery in Visalia, Tulare County, California, as a seedling resulting from a cross between a seed parent, Sister Therese × Wilhelm, and a pollen parent, Caroline Dean × Tom Thumb.

The variety—after its origination, and when grown to maturity—was recognized as being very advantageously distinct in that it was not only an ever-blooming miniature, but a climber; no miniature rose having theretofore been known to have a climbing habit.

Subsequent to its origination the variety was successfully asexually reproduced by me in my nursery located as aforesaid, both by budding and cuttings; all of the asexual reproductions having been found to carry forward the characteristics of the original plant.

In the drawings:

Fig. 2 showing a number of the buds before opening, while Fig. 3 shows certain of the buds as partially open.

Figure 2:
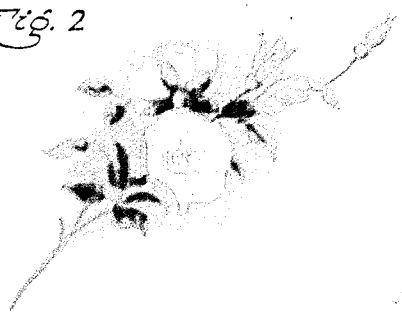
Figs. 2 and 3 are similar but smaller views.
Figure 1:
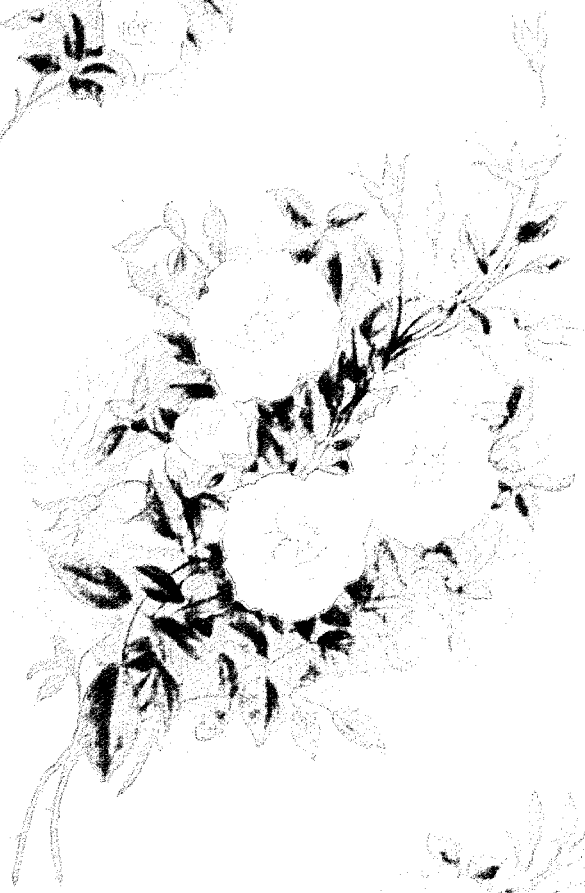
Fig. 1 is an elevation showing a spray of flowers and buds of the variety, together with leaves and stems.
Figure 3:
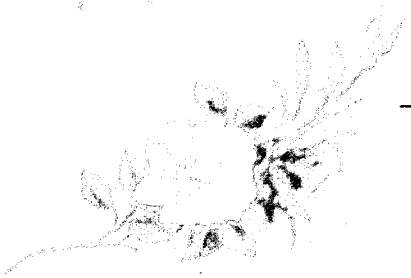

Referring now specifically to the new and distinct variety of rose plant, the following is a detailed description thereof in outline; all major color plate identification being by Maerz and Paul Dictionary of Color.

Type: Climbing; hardy; outdoor; greenhouse; garden decoration; cut flowers.

Class: Miniature climber.

Flowers:

*Continuity.*—Continuous.

*Fragrance.*—Slight.

Flowers borne: Two to three up to fifteen or twenty on strong, medium length stems.

Quantity of bloom: Abundant; outdoors; greenhouse.

Bud:

*Peduncle.*—Long; slender; medium; erect; stiff; medium reddish green; numerous brown hairs.

*Before calyx opens.*—Size—small. Form—pointed. Foliaceous appendages on the surface of the bud. Slender foliaceous parts extending beyond the tip of the bud equal to one-half or more of its length. Color—Green (22–L–8).

*As calyx breaks.*—Color—Pink (1–A–3, shading to 1–A–6).

*As first petal opens.*—Size—very small. Form—pointed; ovoid. Color—Pink (1–A–3, shading to 1–A–6).

Bloom:

*Size.*—Very small. Average diameter—1¼″ to 1⅜″.

*Petalage.*—Double, with from twenty to twenty-five petals arranged regularly.

*Form.*—Full. Petals loosely rolled outward.

Petals: Thick. Satiny both inside and outside.

*Shape.*—Outside—obovate, almost round; intermediate—obovate; inside—obovate.

*Color.*—Soft rose pink—light pink (1–B–1) at tips, shading darker (1–A–3 to 1–A–6) inwardly. Stability—excellent.

*Behavior.*—Old flowers persist for short time, then usually the entire flower drops rather than individual petals.

*Flower longevity.*—Bush in garden—five days, sometimes longer. Cut flowers indoors—five to seven days.

Reproductive organs:

*Stamens.*—Medium number. Arranged regularly about pistils.

*Filaments.*—Short; yellow; most with anthers.

*Anthers.*—Very small; yellow.

*Pollen.*—Sparse; yellow; apparently sterile.

*Pistils.*—Medium number.

*Styles.*—Very short; very thin; bunched.

*Stigma.*—Yellow.

*Ovaries.*—All enclosed in calyx.

*Hips.*—None.

*Seeds.*—None.

Foliage:

*Leaves.*—Compound of three to five leaflets. Normal; small; moderately heavy and glossy.

*Leaflets.*—Ovoid.

*Apex.*—Acute.

*Base.*—Round.

*Margin.*—Serrate.

*Color.*—Top side—medium green (22–L–8); under side—lighter green (21–I–5).

*Rachis.*—Medium. Two or three small brown (6–D–11) thorns.

*Stipules.*—Short; medium width. Long points turning out at an angle of less than 45°.

Growth:

*Habit.*—Climbing, averages four or five feet in height. Branched.

*Growth.*—Vigorous.

*Canes.*—Medium.

*Main stems.*—Green. Thorns—average—several; short; straight; short narrow base. Prickles—none. Hairs—none.

*Branches.* — Green. Thorns — average — several; short; straight; short narrow base. Prickles—none. Hairs—none.

*New shoots.*—Green. Thorns—average—several; short; straight; short narrow base. Prickles—none. Hairs—none.

All of the existing rose varieties hereinbefore mentioned are unpatented, except "Tom Thumb," which is the subject of United States Plant Patent No. 169, and "High Noon," which is the subject of United States Plant Patent No. 704.

The miniature rose plant and its flowers as herein described may vary in slight detail due to climatic and soil conditions under which the variety may be grown.

I claim:

A new and distinct variety of miniature rose plant, substantially as described and illustrated, having an ever-blooming climbing habit, blooming initially when the plant is six to eight inches high; and further characterized by substantially perfectly shaped buds, and pink flowers with double regularly arranged petalage which is full with the petals loosely rolled outward, the flowers being long lasting on the plant and when cut, and having excellent color stability; the plant being readily propagated by budding or cuttings, seedless, and a vigorous grower; and such plant having generally the growth and blooming habits of the High Noon rose, but being distinguished therefrom by being a miniature and bearing pink rather than yellow flowers.

No references cited.